(12) United States Patent
Ho et al.

(10) Patent No.: US 9,764,108 B2
(45) Date of Patent: Sep. 19, 2017

(54) HEADGEAR STRAP MEMBERS WITH ENHANCED COMFORT

(75) Inventors: Peter Chi Fai Ho, Eindhoven (NL); Jerome Matula, Jr., Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 835 days.

(21) Appl. No.: 13/993,184

(22) PCT Filed: Nov. 29, 2011

(86) PCT No.: PCT/IB2011/055355
§ 371 (c)(1),
(2), (4) Date: Jun. 11, 2013

(87) PCT Pub. No.: WO2012/080887
PCT Pub. Date: Jun. 21, 2012

(65) Prior Publication Data
US 2013/0263859 A1    Oct. 10, 2013

Related U.S. Application Data

(60) Provisional application No. 61/422,243, filed on Dec. 13, 2010.

(51) Int. Cl.
*A61M 16/06* (2006.01)
*A62B 18/08* (2006.01)

(52) U.S. Cl.
CPC ........ *A61M 16/0683* (2013.01); *A61M 16/06* (2013.01); *A61M 16/0605* (2014.02); *A62B 18/084* (2013.01)

(58) Field of Classification Search
CPC ....... A61F 9/02; B63C 11/12; A41D 13/1161; A61M 16/0683; A61M 16/0694; A61M 16/06; A61M 16/00; A63B 33/002; A62B 18/08; A61B 33/002
USPC ............ 224/181, 264; 602/75, 78, 79; 2/181
See application file for complete search history.

(56) References Cited

U.S. PATENT DOCUMENTS

| | | | | |
|---|---|---|---|---|
| 2,184,060 A | * | 12/1939 | Singer | A44C 5/0053 224/171 |
| 5,651,763 A | * | 7/1997 | Gates | A61F 5/028 128/876 |
| 8,950,404 B2 | * | 2/2015 | Formica | A61M 16/0683 128/207.11 |
| 2002/0100107 A1 | * | 8/2002 | Shin | A41D 20/00 2/181 |
| 2004/0025882 A1 | | 2/2004 | Madaus | |
| 2008/0053451 A1 | * | 3/2008 | Bordewick | A61M 16/06 128/207.11 |
| 2008/0184678 A1 | | 8/2008 | Chang | |

(Continued)

FOREIGN PATENT DOCUMENTS

| | | |
|---|---|---|
| CN | 101128313 A | 2/2008 |
| CN | 201341565 Y | 11/2009 |

(Continued)

*Primary Examiner* — Justine Yu
*Assistant Examiner* — Douglas Sul
(74) *Attorney, Agent, or Firm* — Michael W. Haas

(57) ABSTRACT

A strap member for use in securing a mask to the head of a patient includes a strap portion formed from a first material. The first material comprises a silicone material. The strap member further includes a breathability enhancing element associated with the strap portion.

7 Claims, 7 Drawing Sheets

(56) References Cited

U.S. PATENT DOCUMENTS

| | | | |
|---|---|---|---|
| 2009/0044808 A1 | 2/2009 | Guney | |
| 2009/0229041 A1* | 9/2009 | Tufenkjian | A42B 3/145 2/414 |
| 2010/0258136 A1* | 10/2010 | Doherty | A61M 16/0666 128/207.17 |
| 2010/0307502 A1* | 12/2010 | Rummery | A61M 16/06 128/205.25 |
| 2010/0319700 A1* | 12/2010 | Ng | A61M 16/06 128/206.28 |

FOREIGN PATENT DOCUMENTS

| | | |
|---|---|---|
| DE | 2613776 A1 | 10/1977 |
| WO | WO0076334 A1 | 12/2000 |
| WO | WO2007125487 A1 | 11/2007 |
| WO | WO2009026627 A1 | 3/2009 |
| WO | WO2009108995 A1 | 9/2009 |

* cited by examiner

HEADGEAR STRAP MEMBERS WITH ENHANCED COMFORT

CROSS-REFERENCE TO RELATED APPLICATIONS

This patent application claims the priority benefit under 35 U.S.C §371 of international patent application no. PCT/IB2011/055355, filed Nov. 29, 2011, which claims the priority benefit under 35 U.S.C. §119(e) of U.S. Provisional Application No. 61/422,243 filed on Dec. 13, 2010, the contents of which are herein incorporated by reference.

BACKGROUND OF THE INVENTION

1. Field of the Invention

The present invention pertains to headgear for use in securing devices, such as respiratory masks to a human head, and, more particularly, to strap members used in such headgear having features to improve the comfort of such strap member when worn by a user.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a respiratory patient interface device including a mask component that is typically secured on the face of a patient by a headgear assembly. The mask component may be, without limitation, a nasal mask that covers the patient's nose, a nasal cushion having nasal prongs that are received within the patient's nares, a nasal/oral mask that covers the nose and mouth, or full face mask that covers the patient's face. It is known to maintain such devices on the face of a wearer by a headgear having one or more straps adapted to fit over/around the patient's head. Because such respiratory patient interface devices are typically worn for an extended period of time, it is important for the headgear to maintain the mask component in a desired position while doing so in a manner that is comfortable to the patient.

One example of such a respiratory patient interface device is the Swift LT available from ResMed Inc. FIG. 1 shows an example of such device, generally indicated as 1, which includes a nasal pillows mask 2 adapted to be secured to a patient's head via headgear 4 as shown. Headgear 4 includes a first strap member 6 coupled to nasal mask 2 and disposed generally about an upper portion of a patient's head. Headgear 4 further includes a second strap member 8 that is coupled to first strap member on either side of a patient's head and is disposed below first strap member at about a mid portion of the rear of a patient's head. Such arrangement is generally adequate for securing the mask to the patient's head but still leaves room for improvement.

SUMMARY OF THE INVENTION

Accordingly, it is an object of the present invention to provide an improved strap member for use in securing a patient interface device to the head of a patient that overcomes the shortcomings of conventional strap members. This object is achieved according to one embodiment of the present invention by providing a strap member that includes a strap portion formed from a silicone material and a breathability enhancing element associated with the strap portion.

BRIEF DESCRIPTION OF THE DRAWINGS

FIG. 2-C and 2D are front and side views of the head of a patient, respectively, identifying examples of particular areas of concern;

FIG. 4-B is a cross-sectional view of the portion of the strap member of FIG. 4-A taken along line 4-B;

FIG. 5-B is a cross-sectional view of the portion of the strap member of FIG. 5-A taken along line 5-B;

DETAILED DESCRIPTION OF EXEMPLARY EMBODIMENTS

Figure 1:
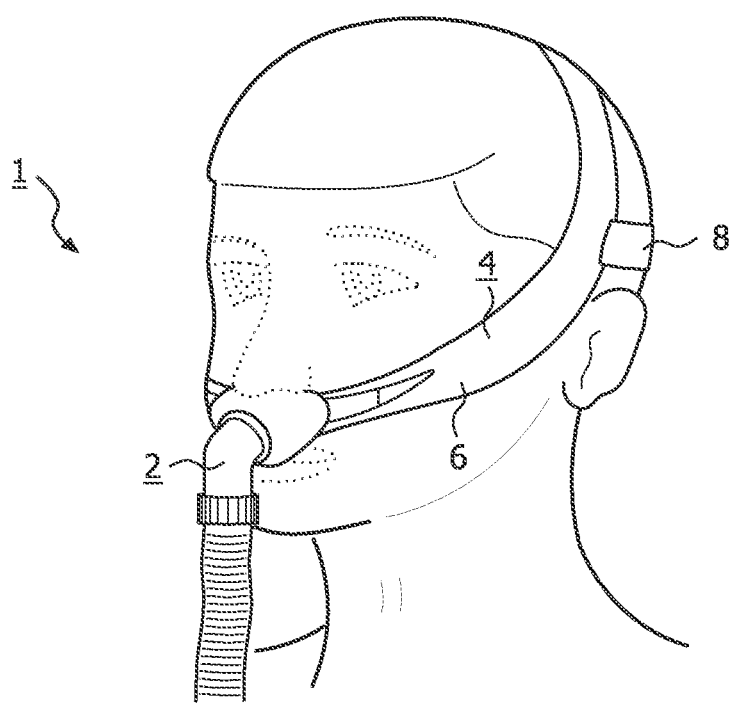
FIG. 1 is an isometric view of a known respiratory patient interface device.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein. Like numbers refer to like elements throughout.

The present invention is directed to the strap member used in a headgear for securing a medical device, such as a mask, to the head of the patient. An example of a such a headgear and strap members includes the patient interface device of FIG. 1. The present invention contemplates that the strap members of the present invention are formed generally from silicone as a unitary piece or strip. However, it is to be understood that the present invention is intended to apply to all flexible straps fabricated from a flexible material with or without stretch-ability. Other common materials that may be employed in place of silicone includes, for example, without limitation, thermoplastic elastomer (TPE), thermoplastic polyurethane (TPU), and vinyl.

The present invention seeks to improve upon a conventional silicon strap (or strap formed from a similar material) by providing one or more breathability enhancing element or weight reduction elements. Silicone or other rubber-like materials used in strap members are often bathers to the skin of the patient that create hot spots and can entrap sweat. Breathability enhancing elements address this problem and provide a mechanism that enables air to pass over the user's skin that is not otherwise possible when using a solid piece of silicon material as the strap member, thereby increasing the "breathabilitiy" of the strap member, i.e., avoiding hot spots and moisture buildup. Weight reducing mechanisms reduce the weight or bulk of material that is on the user's face. Both the breathability enhancing elements and the weight reducing mechanisms attempt to make the headgear more comfortable for the user. The breathability enhancing elements and the weight reducing mechanisms can be used individually or in combination.

Figure 2A:
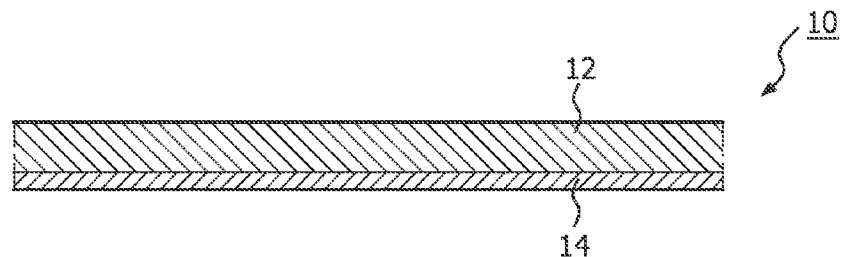
FIGS. 2-A and 2-B are cross-sectional views of portions of strap members that have modified surface properties according to particular embodiments of the present invention.
Figure 2B:
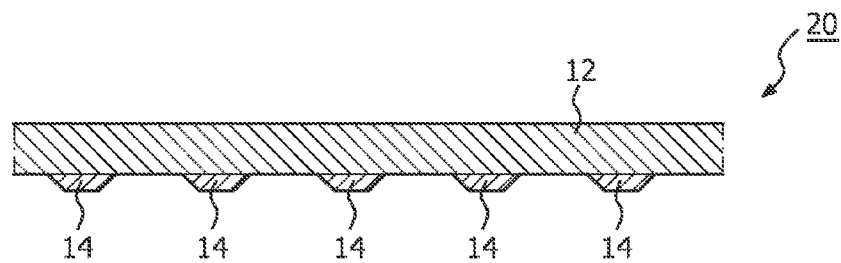
Figures 2C, 2D:
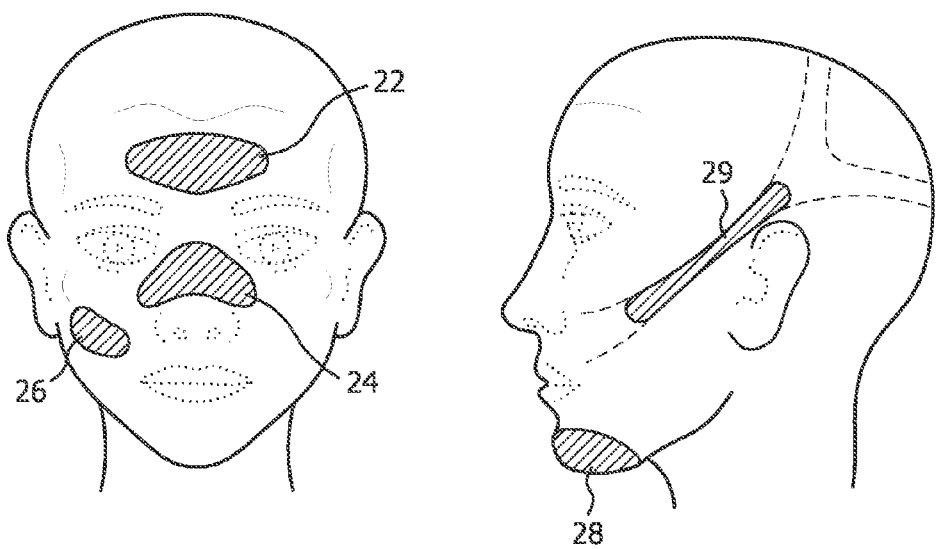

FIGS. 2-A and 2-B illustrate exemplary embodiments of portions of strap members according to the principles of the present invention. FIG. 2-A shows an example embodiment in which a strap member 10 includes a strap portion 12, preferably formed from silicone or other suitable material, that has been coated with a coating 14 as the breathability enhancing element in order to modify the surface properties, such as, for example, without limitation, friction or tactile feel of strap 12. Such coating may comprise, for example, without limitation, silicone, rubber, fabric or other suitable material. Coating 14 may be applied on one side or both sides of silicone strap portion 12 and may be applied to the complete side or applied partially to a side in selected areas, such as shown by the example strap member 20 of FIG. 2-B.

The present invention further contemplates providing a partial coating in a pre-defined pattern to modify surface finish locally at specific locations needed. FIGS. 2-C and 2-D provide some example locations on the head of a patient where increased friction (i.e., grip) of a strap member would be desirable. Such locations may include, for example, without limitation, the forehead area 22, the nose area 24, the cheek or cheekbone area 26, the chin area 28, and the side of the head/temple region 29.

Figure 3:
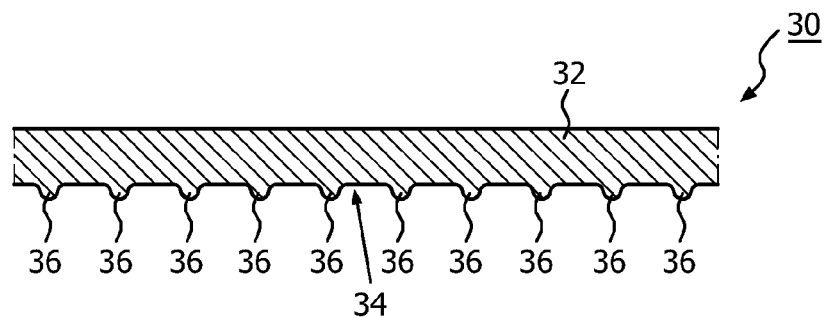
FIG. 3 is a cross-sectional view of a portion of yet another strap member that has modified surface properties according to one particular embodiment of the present invention.

FIG. 3 illustrates another exemplary embodiment of a portion of a strap member 30 according to the principles of the present invention. Similar to strap members 10 and 20 previously discussed, strap member 30 includes a silicone strap portion 32. However, unlike strap members 10 and 20 previously discussed, silicone strap portion 32 is not coated with a material, but instead is itself partially formed into other structures. More particularly, a lower portion 34 of strap portion 32 that abuts the surface of the user during use is formed to include a number of micro bumps 36 as the breathability enhancing element. The micro bumps may be formed as: discrete, generally dome-like bumps; as elongated ridge-like bumps (similar to a speed bump), or any combination thereof. Such structures serve to modify the surface properties of strap member 30, such as the friction or tactile feel of the strap 30. Micro bumps 36 also raise the remainder of the strap off of the surface of the user to allow a flow of air to pass over the user's skin, thereby increasing the "breathabilitiy" of the strap member, i.e., the airflow over the user's skin.

Figure 4A:
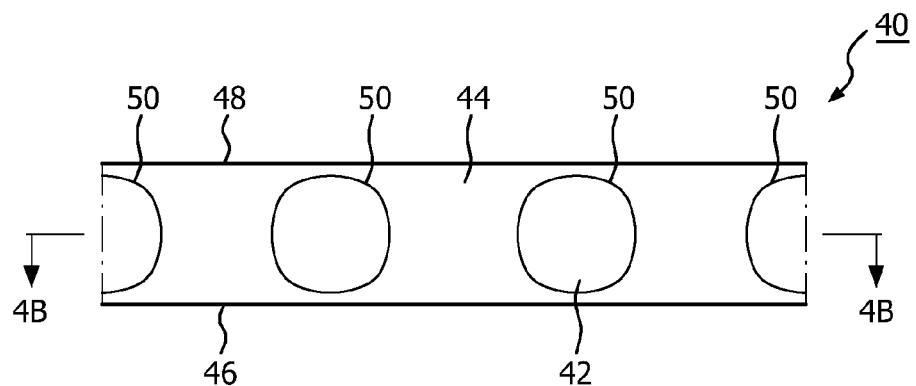
FIG. 4-A is an elevational view of a portion of a strap member that has been modified to change its weight and/or flexibility according to one particular embodiment of the present invention.
Figure 4B:
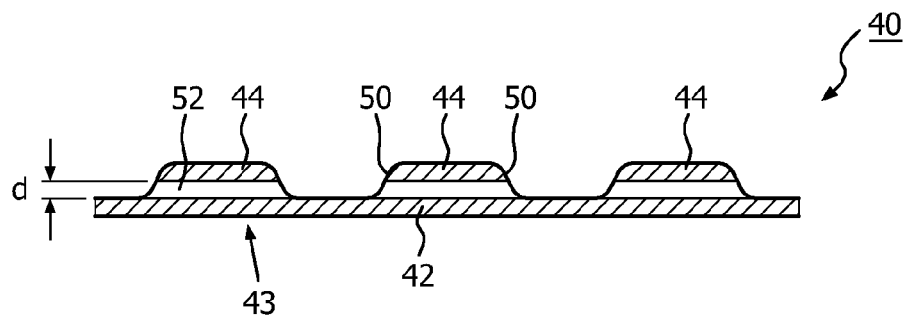

FIGS. 4-A and 4-B illustrate elevational and cross-sectional views, respectively, of another exemplary embodiment of a portion of a strap member 40 according to the principles of the present invention. Strap member 40 is generally formed from lower and upper silicone portions 42, 44 spaced apart by a distance d (FIG. 4-B) that are generally coupled at a first edge 46 and a second edge 48 (FIG. 4-A). A surface 43 of lower portion 42 contacts the surface of the user. Silicone portion 44 includes a number of cut-out portions 50 formed therein that provide access to an air pocket 52 formed in the space generally between lower and upper portions 42 and 44 thus functioning as a weight reduction mechanism. Such structure demonstrates an example embodiment of incorporating hollow sections in a strap to modify the weight of strap. It is generally desirable to reduce the weight of the strap to improve comfort to the user. Such technique of providing hollow sections may also be utilized to modify the flexibility of a strap by varying the size, number, and/or spacing of cut-out portions 50 in a particular location as desired. Although upper portion 44 is shown in FIGS. 4-A and 4-B as being generally circular, is to be understood that other geometries, sizes, numbers, arrangements, and configurations are contemplated for the upper portion and the cut-outs defined therein.

Figure 5A:
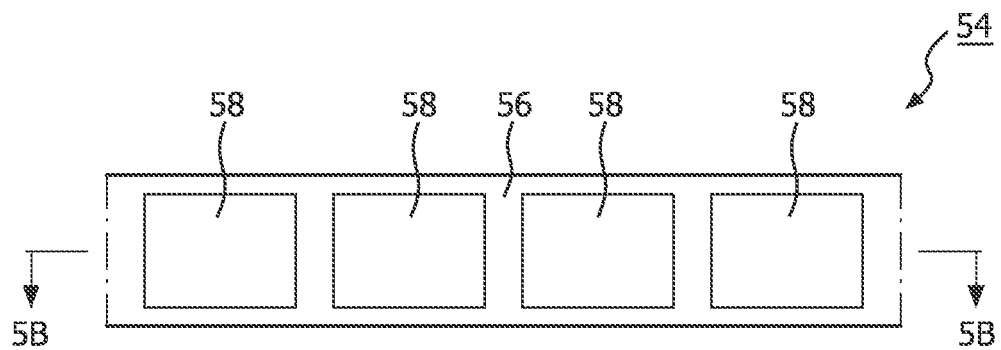
FIG. 5-A is an elevational view of a portion of a strap member that has been modified to change its weight and/or flexibility and/or breathability according to one particular embodiment of the present invention.
Figure 5B:
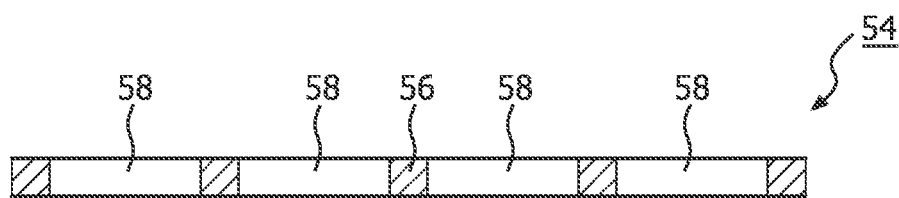

FIGS. 5-A and 5-B illustrate elevational and cross-sectional views, respectively, of another exemplary embodiment of a portion of a strap member 54 according to the principles of the present invention. Strap member 54 is generally formed from a silicone body portion 56 having a number of apertures 58 formed therein. Apertures 58 help to lighted the weight of the strap member and also reduce the amount of skin covered by the strap member, this increasing the breathability. As such, apertures 58 function as both a breathability enhancing element and a weight reduction mechanism. Although shown as generally rectangular in shape, it is to be appreciated that the shape of each aperture 58 may be varied (e.g., without limitation, square, circular, triangular, variable) and is not limited to just such rectangular shape. Furthermore, it is to be appreciated that one or more of the size, positioning and quantity of such apertures 58 may be selectively varied to tailor one or more of the weight, breathability and relative stiffness of strap member 54 to meet the desired needs of a particular application.

Figure 6:
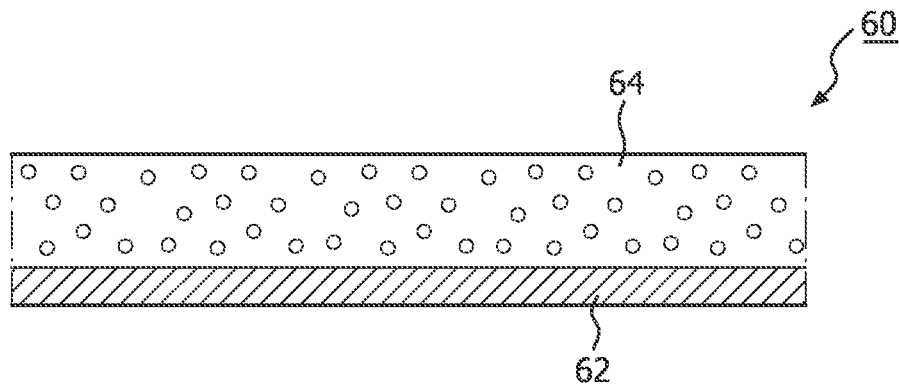
FIG. 6 is a cross-sectional view of a portion of another strap member that has been modified to change its weight and/or flexibility according to one particular embodiment of the present invention.

FIG. 6 illustrates an exemplary embodiment of another strap member 60 that has also been modified to change its weight and/or flexibility according to the principles of the present invention. More particularly, strap member 60 includes a silicone strap portion 62 and a layer of silicone foam 64 bonded thereto as a weight reduction mechanism. Such composite construction can be used to provide a strap member that provides desired properties of silicone but at a lesser weight than a strap member formed solely of silicone.

Figure 7A:
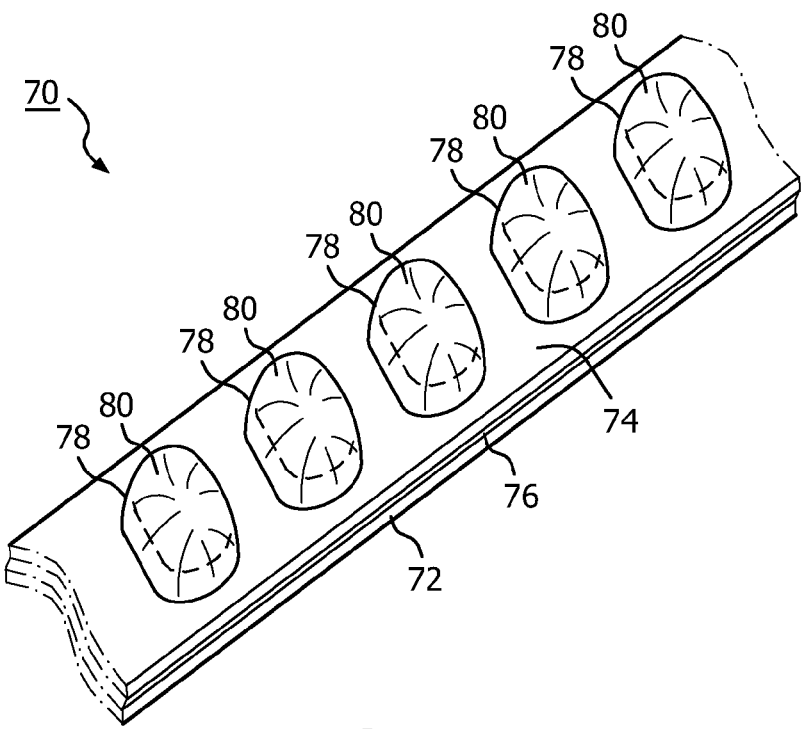
FIGS. 7-A, 7-B and 7-C are isometric, elevation, and cross-sectional views, respectively, of a portion of a strap member according to a particular embodiment of the present invention.
Figure 7B:
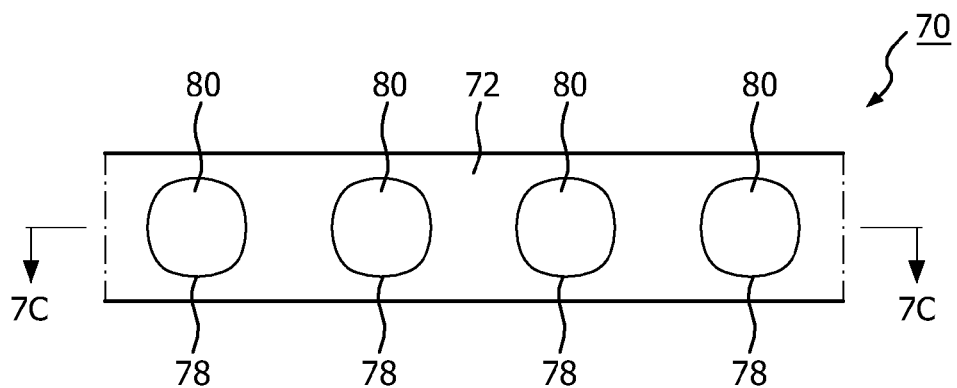
Figure 7C:
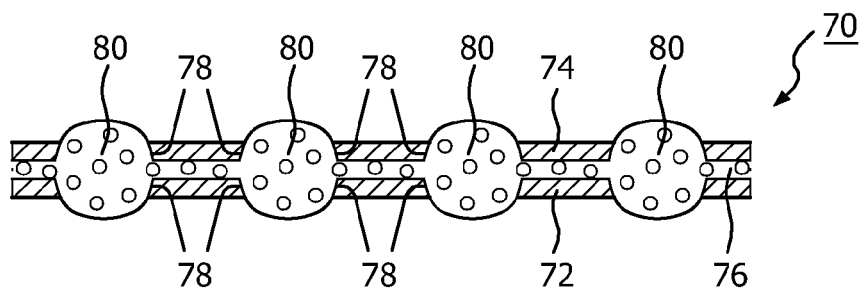

FIGS. 7-A, 7-B and 7-C illustrate isometric, elevation, and cross-sectional views of an exemplary embodiment of a portion of a strap member 70 formed generally as a composite sandwich structure according to the principles of the present invention. Strap member 70 is generally formed from lower and upper portions or layers 72, 74, preferably formed from silicone or other suitable material, with a mid portion or layer 76 disposed therebetween. Layer 76 is preferably formed from a softer medium than layers 72 and 74, such as, for example, without limitation, fabric or foam. Lower and upper portions 72, 74 include a number of cut-out portions 78 through which selected portions 80 of mid portion 76 may protrude and thus contact the skin of a patient. As can be appreciated from the explanation below, layer 76 functions as a breathability enhancing element.

Although shown as being in both lower and upper portions 72 and 74, cut-out portions 78 may also be formed in only one of the lower and upper portions 72, 74. Additionally, another variation of strap member 70 is formed without upper portion 74. In such embodiment, strap member 70 includes only lower portion 72 and mid portion 76. Such embodiments may be employed to modify the surface properties such as friction or feel of the strap member 70. Additionally, such arrangement may be employed to improve the breathability of the strap member by one or both of elevating outer silicone portion (72 or 74) from the skin of a patient and/or by providing a generally porous pathway through the strap member 70.

Figure 8:
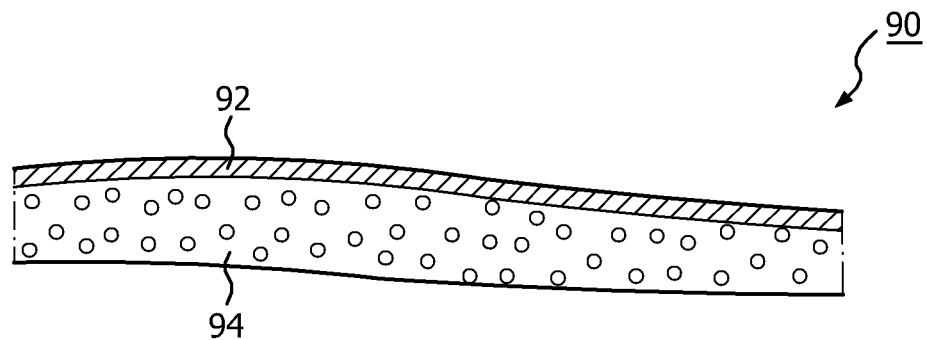
FIGS. 8-10 are cross-sectional views of portions of strap members that have been modified to improve comfort to a user according to particular embodiments of the present invention.
Figure 9:
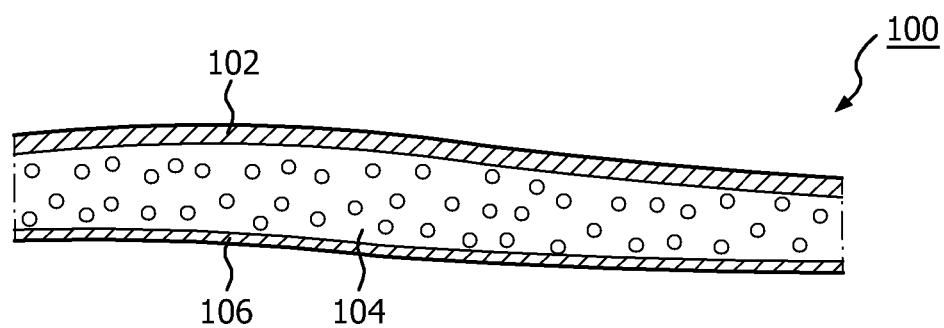
Figure 10:
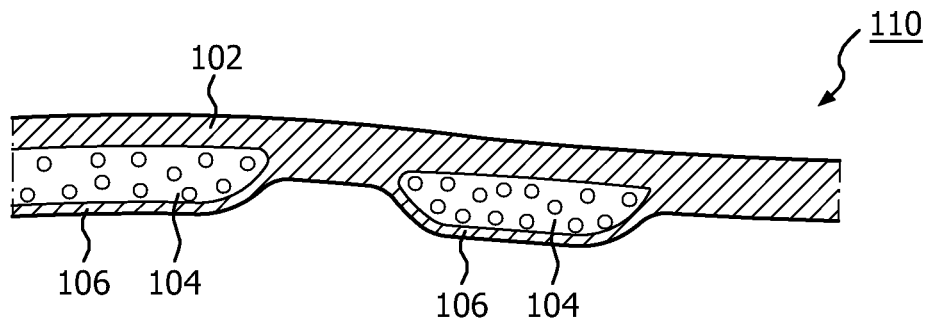

FIGS. 8, 9 and 10 illustrate cross-sectional views of portions of exemplary strap members 90, 100 and 110 according to the principles of the present invention. Referring to FIG. 8, strap 90 includes a strap portion 92, preferably formed from silicone or other suitable material, that has been coated with a coating 94, preferably a gel or other similar material. The gel in this embodiment is applied to one side of strap portion 92 without encapsulation. In use, the gel provides a certain stickiness to encourage strap 90 to stay in place on the human body.

Referring to FIG. 9, strap 100 includes a strap portion 102, preferably formed from silicone or other suitable material, and a secondary material 104, preferably formed from a gel or other similar material, that is encapsulated in a layer 106 of silicone or other suitable material. The structure of strap 100 enhances comfort and conformability of the strap. As an alternative to strap 100 in which all, or at least a large section a strap is filled with secondary material 104, FIG. 10 illustrates an example strap member 110 wherein secondary material 104 is selectively segregated into generally smaller portions 108. Other media such, for example, without limitation, water or air, may be used in as secondary material to modify the feel and comfort of straps 100 or 110.

Figure 11A:
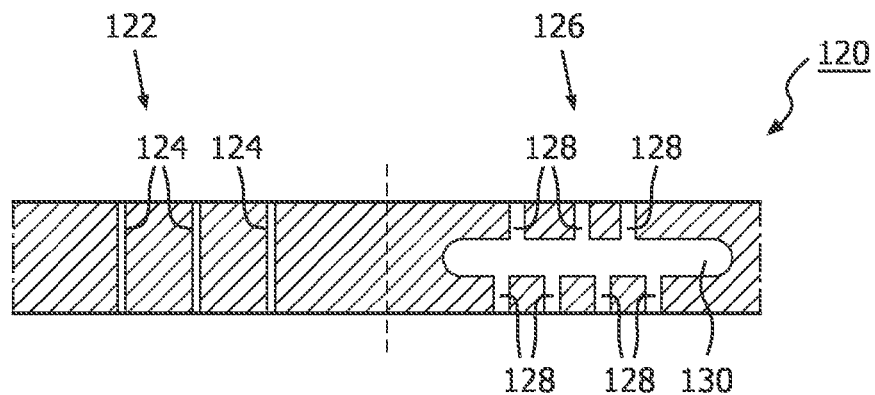
FIGS. 11-A and 11-B are cross-sectional and elevational views of a portion of a strap members according to a particular embodiment of the present invention.
Figure 11B:
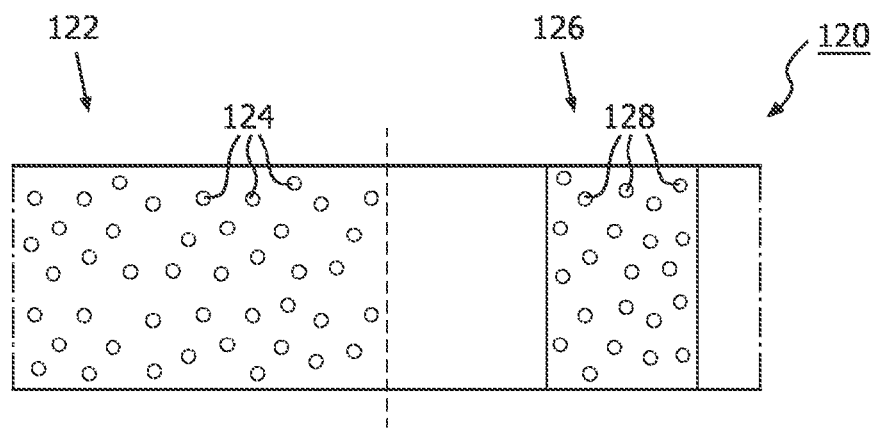

FIGS. 11-A and 11-B illustrate cross-sectional and elevational views, respectively, of an exemplary embodiment of a portion of a strap member 120 according to the principles of the present invention. The left portion 122 of strap member 120 demonstrates an embodiment including a number of micro holes or apertures 124 acting as a breathability enhancing element. Apertures 124 extend through strap 120 to provide a pathway through which air or sweat may pass. The right portion 126 of strap member 120 demonstrates an embodiment including a number of micro holes or apertures 128 that extend partially in strap member 120 to a reservoir 130 disposed within strap member 120. Through the use of such structures, strap 120 becomes "breathable", and thus more comfortable to a user.

It can be appreciated from the foregoing that the present invention provides improvements to solid piece strap members used in headgear formed from silicone or similar material. These improvements enhance the comfort of the strap member on the user. In particular, the present invention provides improved "breathability" to enable the user's skin under the strap member to remain dry with access to a flow of air and/or reduce the weight of the strap member. To the extent possible, each of the breathability enhancing elements can be used in combination with one or more of the other breathability enhancing elements and/or weight reduction mechanisms. Similarly, to the extent possible, each of the weight reduction mechanisms can be used in combination with one or more of the other weight reduction mechanisms and/or breathability enhancing elements.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A strap member for use in securing a mask to the head of a patient, the strap member comprising:
   a strap portion formed from a first material, the first material comprising a silicone material; and
   a breathability enhancing element associated with the strap portion,
   wherein the breathability enhancing element comprises a reservoir disposed within the strap portion, the reservoir being in communication with a first side of the strap portion via a first number of apertures disposed on a first side of the reservoir and in communication with a second side of the strap portion, opposite the first side of the strap portion, via a second number of apertures disposed on a second side of the reservoir opposite the first side of the reservoir, the first number of apertures, second number of apertures, and the reservoir being adapted to provide a passageway allowing air to pass through the strap portion; and
   wherein the reservoir is devoid of any material aside from ambient air.

2. A strap member for use in securing a mask to the head of a patient, the strap member comprising:

a strap portion formed from a first material, the strap portion having a first outer surface structured to be disposed in contact with the head of the patient and a second outer surface disposed opposite the first outer surface; and a reservoir defined within the strap portion, the reservoir being in communication with the first outer surface via a first number of apertures and in communication with the second outer surface of the strap portion, opposite the first side via a second number of apertures, the first number of apertures, second number of apertures, and the reservoir being adapted to provide a passageway allowing air to pass through the strap portion; and wherein the reservoir is devoid of any material aside from ambient air.

3. The strap member of claim 2, wherein the first material comprises a silicone material.

4. The strap member of claim 2, wherein the first number of apertures are disposed on a first side of the reservoir and wherein the second number of apertures are disposed on a second side, opposite the first side of the reservoir.

5. The strap member of claim 2, wherein at least one of the first number of apertures and the second number of apertures comprises a plurality of apertures.

6. The strap member of claim 2, wherein the first number of apertures comprises a plurality of apertures and wherein the second number of apertures comprises a plurality of apertures.

7. The strap member of claim 2, wherein the reservoir is separated from the first outer surface by a first portion of the strap portion; wherein the reservoir is separated from the second outer surface by a second portion of the strap portion; and wherein the first portion and the second portion are disposed on opposite sides of the reservoir.

* * * * *